(12) United States Patent
Kleyman et al.

(10) Patent No.: US 11,779,707 B2
(45) Date of Patent: Oct. 10, 2023

(54) SYRINGE PLUNGER FINGER RING STRUCTURES

(71) Applicants: Gennady I Kleyman, Brooklyn, NY (US); Alexander Merson, Brooklyn, NY (US)

(72) Inventors: Gennady I Kleyman, Brooklyn, NY (US); Alexander Merson, Brooklyn, NY (US)

(73) Assignee: Alger & Klemer, L.L.C., New York, NY (US)

( * ) Notice: Subject to any disclaimer, the term of this patent is extended or adjusted under 35 U.S.C. 154(b) by 136 days.

(21) Appl. No.: 17/228,797

(22) Filed: Apr. 13, 2021

(65) Prior Publication Data

US 2022/0203035 A1 Jun. 30, 2022

Related U.S. Application Data

(62) Division of application No. 17/137,490, filed on Dec. 30, 2020, now Pat. No. 11,534,552.

(51) Int. Cl.
*A61M 5/31* (2006.01)

(52) U.S. Cl.
CPC ........ *A61M 5/3137* (2013.01); *A61M 5/3148* (2013.01); *A61M 2005/3139* (2013.01); *A61M 2210/0637* (2013.01)

(58) Field of Classification Search
CPC ................ A61M 5/3137; A61M 2005/3139
See application file for complete search history.

(56) References Cited

U.S. PATENT DOCUMENTS

| | | | | |
|---|---|---|---|---|
| 2,842,128 | A | * | 7/1958 | Hein, Jr. .............. A61M 5/315 604/227 |
| 5,833,668 | A | * | 11/1998 | Aguilar .............. A61M 5/3135 604/227 |
| 2007/0208310 | A1 | * | 9/2007 | Stadick .............. A61M 5/3148 604/187 |
| 2009/0093787 | A1 | * | 4/2009 | Barbour ............. A61M 5/3137 604/207 |

* cited by examiner

*Primary Examiner* — Amber R Stiles
*Assistant Examiner* — Hong-Van N Trinh

(57) ABSTRACT

A syringe finger ring and finger ring inserts, that in various embodiments, provides or connects to a syringe that comprises a syringe body capable of having a volume of material therein and a plunger disposed to enter the syringe body and dispense material from the syringe body by movement of plunger, and a novel a finger ring related structures having an open area and connected, by various structures, to the plunger adapted to receive a finger within the finger ring open area, including a spacer of various embodiments inserted within the open area to selectively reduce the open area and provide more controllable engagement of the syringe plunger by the operator finger in distal and proximal strokes.

4 Claims, 2 Drawing Sheets

SYRINGE PLUNGER FINGER RING STRUCTURES

Priority is claimed on Non-Provisional patent application Ser. No. 17/137,490 filed 30 Dec. 2020, entitled Syringe Plunger Finger Ring Structures and Provisional Patent Application No. 63/071,409 filed 28 Aug. 2020, entitled Adjustable Ring Structure For Dental Syringe.

FIELD OF THE INVENTION

The present invention relates to syringes in particular, to conventional and dental syringes having finger receptacle to better engage operator finger to facilitate comfortable use of the syringes.

BACKGROUND OF THE INVENTION

Conventional and dental syringe used requires skilled and confident, accurate operation (e.g. a controlled compression of a syringe plunger) and simultaneous precise control of the needle location and depth. Moreover, it is very important to precisely accomplish both the distal (injecting) stroke, e.g. to determine whether the needle is in a blood vessel, and the proximal (aspirating) stroke. These qualities are absolutely necessary in cosmetic procedure applications (injection of Botox, fillers etc) and in dental procedures. Existing conventional and dental syringes typically have limited plunger ring surfaces. This drawback makes it hard to operate and hard to control the dispensing of syringe content. It is also very important to emphasize that the plunger ring surfaces of existing syringes don't accommodate the variety of finger sizes, and don't have any structure to enhance the operation itself or to control of syringes by the user.

SUMMARY OF THE INVENTION

Disclosed is an ergonomically improved conventional and dental syringe including adjustable ring structure that substantially surround the operator finger with portions of the syringe member that receives an operator finger, which facilitates to operate the plunger conveniently and more controllably to accomplish both the distal (injecting) stroke and the proximal (aspirating) stroke.

In various embodiments, the present invention provides or connects to a syringe that comprises a syringe body capable of having a volume of material therein and a plunger disposed to enter the syringe body and dispense material from the syringe body by movement of plunger, and a novel finger ring and related structures having an open area and connected to the plunger adapted to receive a finger within the finger ring open area, including a spacer of various embodiments inserted within the open area to selectively reduce the open area and provide more controllable engagement of the syringe plunger by the operator finger.

Those embodiments make the syringe significantly more easy, predictable, and controllable to use with both the distal (injecting) stroke and the proximal (aspirating) stroke. The result is a syringe and syringe attachment(s) which enables a reliable and controlled aspiration maneuver and to perform delicate but routine actions, e.g. to test for the presence of blood indicating that a blood vessel has been penetrated, and other critical operations, easily and controllably with one hand.

BRIEF DESCRIPTION OF THE DRAWINGS AND POSITIONS

These and further novel features of the present invention are better understood by taking the following Drawing figures together with the Detailed Description, wherein.

DETAILED DESCRIPTION

Figure 1:
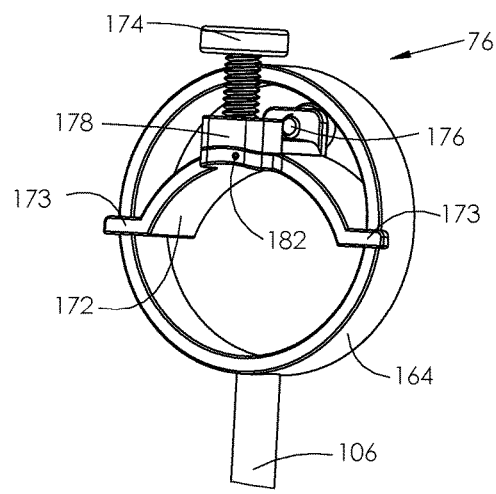
FIG. 1 is an isometric view of ring assembly of an embodiment.
Figure 2:
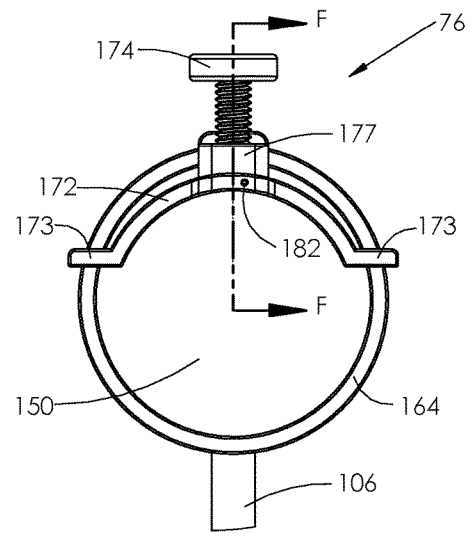
FIG. 2 is a front view of ring assembly of an embodiment.
Figure 3:
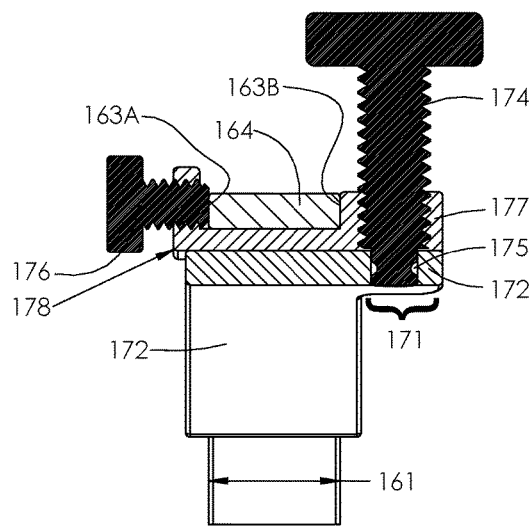
FIG. 3 is a sectional view F-F taken of the embodiment of FIG. 2.
Figure 4:
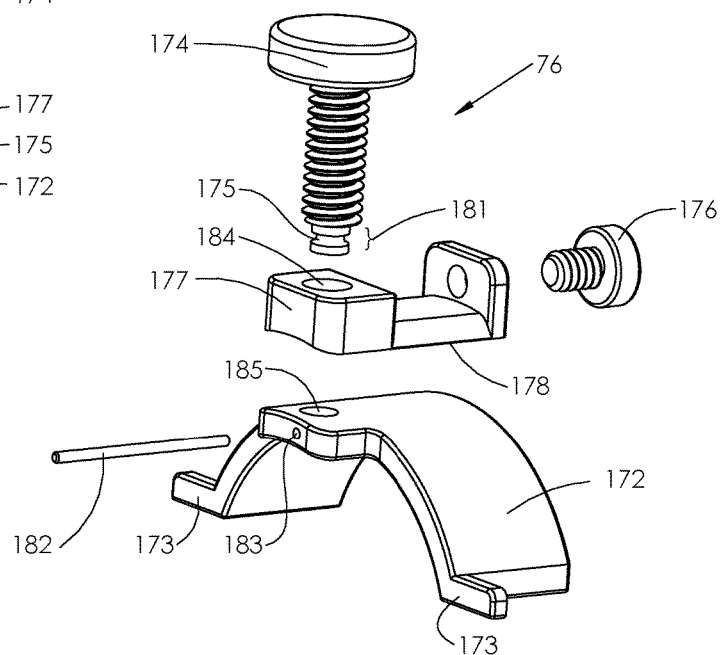
FIG. 4 is an exploded view of insert assembly of the embodiment.

An embodiment 76 is shown in FIGS. 1-4, that includes a screw 174 adjustment of an insertable inner spacer comprising a curved member 172 relative to a threaded holding block 178 within the finger ring comprising an annular member 164 open area 150 having a radial direction extending across the open area 150, and retained by a holding block retaining screw 176, that holding block 178 engages a finger ring longitudinal width formed between a lateral edge 163A of the annular member 164 connected to plunger shaft 106, and the opposing edge 163B by screw 174 threaded shoulder 177 to engage—the finger ring. The lateral movement (in the direction of longitudinal width 161, FIG. 3) is limited by radially outward extending 'ears' 173 attached to one side of curved member 172 to allow insertion of the assembly of the holding block 178, screw 174, and curved member 172 into the open area 150 of the annular member 164. As shown in FIG. 3 cross-section F of FIG. 2, and exploded view of FIG. 4, the screw end 181 received into lateral extension 171 opening 185, having an circumferential recess 175, is captured by a pin 182 inserted into a curved member 172 lateral extension 171 hole 183 that is disposed sufficiently offset from the center of the lateral extension 171 opening 184 to permit pin 182 to tangentially engage the screw annular recess 175 to retain the screw 174 within the lateral extension 171 hole 183, yet permit rotation that allows the screw 174 to move through threaded shoulder 177 by rotation of the screw 174 causing the curved member 172 to advance into (or retract from) the open area to 'fit' the ring 76 to a particular finger. The curved member 172 is moved inward into the open area 150 and retained there by rotation of the screw 174 and limited in lateral motion by the ears 173, providing a close fitting to and retention by a finger inserted into the open area 150.

Figure 5:
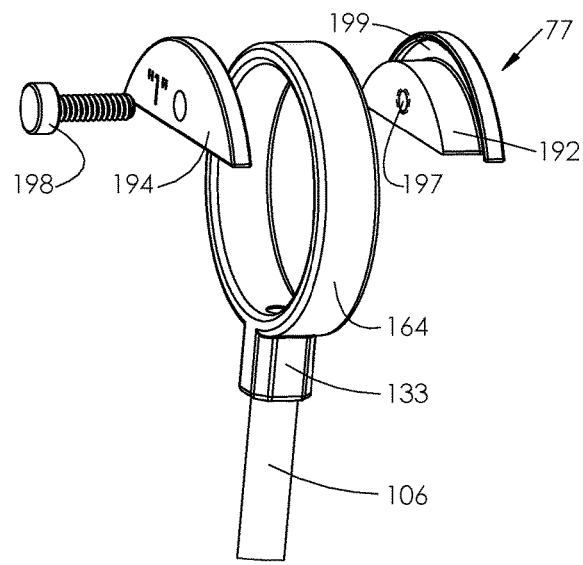
FIG. 5 is an exploded view of inserts assembly with the ring of an alternate embodiment.
Figure 6:
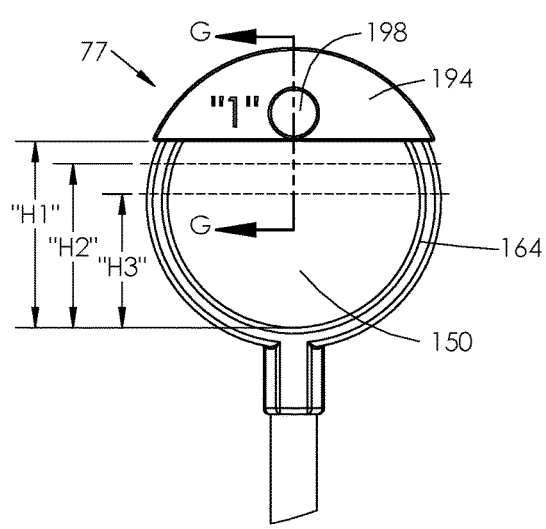
FIG. 6 is a front elevation view of inserts assembled with the ring of the alternate embodiment.
Figure 7:
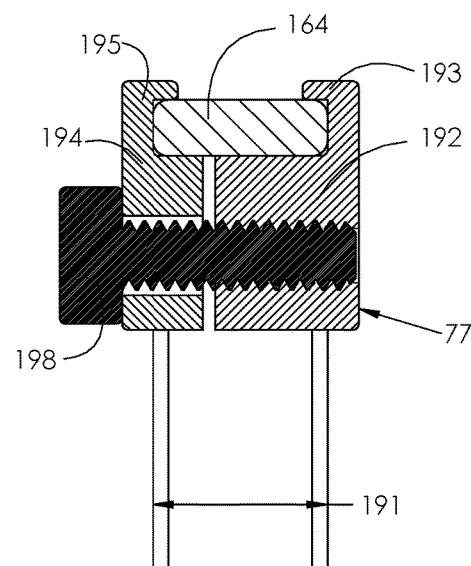
FIG. 7 is a sectional view G-G taken from FIG. 6 of the alternate embodiment.

An alternate embodiment 77 is shown in FIGS. 5-7 that comprises the finger ring or annular member 164 connected to a syringe plunger shaft 106 via a shoulder 133 and has a lateral width 191, around which facing spacers 192, 194 that have a radial dimension into the open area, and are applied to together grip (by radially extending members 193, 195) the annular member 164 longitudinal width as defined above, when a screw 198 engages a threaded opening 197 (or other device) draws the spacing members, or spacers 192, 194 together and apply a compression force to the annular member 164. Typically, the facing spacers, e.g. 194 may also be a segment shape as shown in FIGS. 5 and 6, and may also form a recess e.g. 199, by radially extending members 193, 195 that extend radially outward past the annular member 164, and as shown in cross section G of FIG. 7, and can partially surround the annular member 164. According to embodiments of the present invention, spacers 192, 194 may have a larger inwardly facing dimension to intrude further into the open area 150 to provide different interior spacings, e.g. H1, H2, H3, etc. as desired.

The components of the rigid or semi-rigid embodiments described herein can be fabricated by injection molding from different plastics such as Polypropylene, ABS, Polycarbonate or other materials that can be formed and function as described herein. Further embodiments, modifications and substitutions by one of ordinary skill in the art are within the scope of the present invention which is not limited except according to the claims as follows.

What is claimed is:

1. An apparatus attachable to a syringe plunger shaft, comprising:

an annular member having an open area therein, a radial dimension extending across said open area and a longitudinal width perpendicular to said radial dimension;

facing spacers each having a surface disposed within said open area to provide reduction in said open area, each of said facing spacers further comprising a radially outward extending member, enabling said facing spacers to be retained on said annular member within said open area, wherein each radially outward extending member engages said longitudinal width and comprises longitudinally opposing members applied to opposing edges of said longitudinal width.

2. The apparatus of claim 1, wherein each facing spacer includes an external portion to partially surround said annular member.

3. The apparatus of claim 2, further including a screw configured to draw said facing spacers together.

4. The apparatus of claim 1, wherein each facing spacer comprises a curved segment member.

* * * * *